(12) United States Patent
Sias et al.

(10) Patent No.: US 6,706,243 B1
(45) Date of Patent: Mar. 16, 2004

(54) APPARATUS AND METHOD FOR CLEANING PARTICULATE MATTER AND CHEMICAL CONTAMINANTS FROM A HAND

(75) Inventors: Ralph M. Sias, Oceanside, CA (US); Heath E. Sias, San Marcos, CA (US); Marvin Foster, San Diego, CA (US); Therese Stewart, Wellington, FL (US)

(73) Assignee: Intecon Systems, Inc., Carlsbad, CA (US)

( * ) Notice: Subject to any disclaimer, the term of this patent is extended or adjusted under 35 U.S.C. 154(b) by 0 days.

(21) Appl. No.: 09/564,290

(22) Filed: May 3, 2000

Related U.S. Application Data

(63) Continuation-in-part of application No. 09/306,519, filed on May 6, 1999, now Pat. No. 6,343,425.

(51) Int. Cl.[7] .............................. B08B 3/02; A61L 2/18
(52) U.S. Cl. .................... 422/28; 134/56 R; 134/102.2; 134/102.3; 604/289; 422/292
(58) Field of Search .................. 422/28, 292; 134/95.2, 134/95.3, 30, 57 R, 102.2, 102.3, 200, 201; 604/289

(56) References Cited

U.S. PATENT DOCUMENTS

| | | | |
|---|---|---|---|
| 3,992,221 A | 11/1976 | Homsy et al. ................. 134/16 |
| 4,366,125 A | 12/1982 | Kodera et al. ............... 422/295 |
| 4,643,876 A | 2/1987 | Jacobs et al. .................. 422/23 |
| 4,670,010 A | 6/1987 | Dragone ....................... 604/289 |
| 4,817,800 A | 4/1989 | Williams et al. ............. 206/484 |
| 4,818,488 A | 4/1989 | Jacob ............................ 422/23 |
| 5,058,785 A | 10/1991 | Rich et al. .................... 223/111 |
| 5,074,322 A | 12/1991 | Jaw ........................... 134/56 R |
| 5,084,239 A | 1/1992 | Moulton et al. ............... 422/22 |
| 5,095,925 A | 3/1992 | Elledge et al. ................ 134/61 |
| 5,115,166 A | 5/1992 | Campbell ............... 315/111.23 |
| 5,141,803 A * | 8/1992 | Pregozen ..................... 442/123 |
| 5,178,829 A | 1/1993 | Moulton et al. ............... 422/23 |
| 5,184,046 A | 2/1993 | Campbell ............... 315/111.21 |
| 5,288,460 A | 2/1994 | Caputo et al. ................. 422/23 |
| 5,393,490 A | 2/1995 | Jacob ........................... 422/22 |

(List continued on next page.)

FOREIGN PATENT DOCUMENTS

| | | |
|---|---|---|
| RU | 2021820 C1 * | 10/1994 |
| WO | WO 96/26795 * | 9/1996 |

OTHER PUBLICATIONS

Giles Dillingham et al., "Plasma Processing", PC, Dec. 1998, pp. 10–15.
"University–backed project shoots for 'green' cleaning breakthrougth", Micro, Apr. 1999, pp. 12–17.
Lynn Kuntz, "Ingredients to Raise the Microbial Bar", Food Product, Apr. 1999, Internet publication at http://www.food-productdesign.com/current/0499ap.html, pp. 1–8.

Primary Examiner—Robert J. Warden, Sr.
Assistant Examiner—Sean E. Conley
(74) Attorney, Agent, or Firm—Jones, Tullar & Cooper, PC

(57) ABSTRACT

An apparatus has a hand-cleaning volume sized to receive a gloved or ungloved human hand. The apparatus includes a mechanical-cleaning device and a chemical-cleaning device, operated sequentially to remove particles and chemical contaminants such as organics. The mechanical-cleaning device has a pressurized gas source positioned to direct a flow of pressurized activated gas into the hand-cleaning volume, and a gas-source vent communicating with the hand-cleaning volume to remove the pressurized activated gas after it has passed over the hand. The chemical-cleaning device has an activating nebulizer operable to emit an activated cleaning mist into the hand-cleaning volume so that the activated cleaning mist contacts the hand in the hand-cleaning volume. The hand is cleaned by directing a flow of pressurized ionized gas over the hand, and thereafter flowing a mist of activated cleaning solution over the hand. The cleaning solution preferably includes hydrogen peroxide.

15 Claims, 11 Drawing Sheets

U.S. PATENT DOCUMENTS

| | | |
|---|---|---|
| 5,516,369 A | 5/1996 | Lur et al. ................. 134/1.3 |
| 5,604,993 A | 2/1997 | Auckerman ................. 34/104 |
| 5,622,595 A | 4/1997 | Gupta et al. ................. 438/710 |
| 5,667,753 A | 9/1997 | Jacobs et al. ................. 422/99 |
| 5,700,327 A | 12/1997 | Babacz et al. ................. 134/1.1 |
| 5,750,072 A | 5/1998 | Sangster ................. 422/22 |
| 5,770,000 A | 6/1998 | Zinman et al. ................. 156/345 |
| 5,858,108 A | 1/1999 | Hwang ................. 134/1.3 |
| 5,876,666 A | 3/1999 | Lin et al. ................. 422/29 |
| 5,882,611 A | 3/1999 | Williams et al. ................. 422/292 |
| 5,935,339 A | 8/1999 | Henderson et al. ................. 134/1 |
| 5,942,438 A | 8/1999 | Antonoplos et al. ................. 436/1 |
| 5,975,094 A | 11/1999 | Shurtliff ................. 134/1.3 |
| 5,983,704 A | 11/1999 | Park et al. ................. 73/28.01 |
| 6,017,397 A * | 1/2000 | Doran ................. 134/1 |
| 6,017,414 A | 1/2000 | Koemtzopoulos ................. 156/345 |
| 6,062,976 A | 5/2000 | De Guzman ................. 454/187 |
| 6,431,189 B1 * | 8/2002 | Deibert ................. 134/57 R |

* cited by examiner

APPARATUS AND METHOD FOR CLEANING PARTICULATE MATTER AND CHEMICAL CONTAMINANTS FROM A HAND

This application is a continuation-in-part of application Ser. No. 09/306,519, filed May 6, 1999 now U.S. Pat. No. 6,343,425, for which priority is claimed and whose disclosure is incorporated by reference.

This invention relates to the cleaning of gloved or ungloved hands, and to the measurement of the state of cleanliness of the hands.

BACKGROUND OF THE INVENTION

Workers in a wide range of fields must be certain that their hands are clean. In some cases, the workers wear gloves and in other cases they do not. For example, contaminants on the gloved hands of clean-room workers who work with microelectronic devices may have adverse consequences on product yields. Contaminants on the gloved or ungloved hands of medical and dental workers may transmit infections between patients or may contaminate apparatus. Contaminants on the gloved or ungloved hands of food-service workers may transmit diseases to customers.

The usual approach to hand cleaning in medical, dental, and food-service areas is a thorough washing in water with soap or a comparable disinfectant, and thorough drying. Where gloves are used, the gloves are changed. Such procedures are often mandated. However, studies have shown that in many cases medical, dental, and food-service workers do not follow the rules and do not avail themselves of the opportunity to wash their hands or change gloves, because it is inconvenient and time consuming to interrupt a task to wash and dry the hands or to change gloves. In the microelectronics fabrication field, workers are required to change gloves on a regular schedule, which is expensive in both glove costs and labor down-time.

The practice of wearing gloves has become increasingly widespread in these and other situations, to protect the workers, to protect the material being handled, and to protect third parties. The gloves, which are typically latex or a synthetic material, are cleaned and packaged by glove manufacturers or laundries, but may become contaminated with particles during shipping and storage. Elastomeric gloves are subject to surface hardening and microcracking. The microcracking allows particulate matter to be created and/or trapped at the microcracks. The particulate matter may later detach from the microcracks and surfaces of the gloves. The gloves may also become contaminated with biological organisms during use.

Thus, the failure to completely clean gloved or ungloved hands, and the costs associated with both cleaning the hands and failing to clean the hands, leads to problems in a wide range of fields. There is a need to improve the convenience and reduce the costs associated with the necessary cleaning of gloved or ungloved hands in clean room, medical, laboratory, food-service, and other environments. The present invention fulfills this need, and further provides related advantages.

SUMMARY OF THE INVENTION

The present invention provides an apparatus and method for cleaning gloved and ungloved hands to reduce the particulate content and surface chemical and biological contaminants to acceptable levels, and for measuring the particulate and/or contaminant content found on the surface of the gloved or ungloved hand. The apparatus may be readily used in clean room, medical, laboratory, food service, and other environments. It is a free-standing, self-contained unit except for a power connection, and does not require plumbing or drain connections. (The apparatus may be battery powered, and in that case does not even require an external power connection.) After cleaning of the gloved or ungloved hands, which usually requires less than 30 seconds, the gloved or ungloved hand is dry, so that the worker may immediately return to the activity which requires the cleaned hands. In applications involving gloved hands, the approach of the invention reduces the need to change gloves on a regular basis or, alternatively stated, increases the time between required changing of the gloves. The apparatus may also be used to monitor the number of times each person cleans the hands or changes gloves, and to correlate this information with manufacturing yields, health, or other parameters of interest.

In accordance with the invention, an apparatus has a hand-cleaning volume sized to receive a human hand therein. The apparatus comprises a mechanical-cleaning device including a pressurized gas source positioned to direct a flow of pressurized gas into the hand-cleaning volume, a source of pressurized gas in communication with an inlet of the pressurized gas source, and, optionally, a gas-source vent communicating with the hand-cleaning volume. The pressurized gas is an activated gas either in the form of an ionized gas or a plasma gas, but most preferably balanced ionized air. The flow of activated gas dislodges particles from the surface of the gloved or ungloved hand, and the activated gas aids in repelling the dislodged particles from the surface of the hand so that they do not redeposit thereon. The pressurized gas source may be a gas knife, such as an air knife in the form of a moving sheet of gas that sweeps over the surface of the hand, or a properly positioned set of nozzles that produce a turbulent atmosphere. The pressurized gas flow is preferably pulsed to increase the particle dislodging effects. The mechanical-cleaning device may include a particle counter in the gas-source vent to count particles dislodged from the gloved or ungloved hand. The particle count is interpreted as an indication of the cleanliness of the hands in respect to particles. The pressurized-gas source may also be operated to dry the gloved or ungloved hands after subsequent treatments.

The apparatus also includes a chemical-cleaning device. The chemical-cleaning device removes chemical and/or biological contaminants that may have adhered to the surface of the gloved or ungloved hand during prior use, but whose surface concentration must be reduced. The chemical-cleaning device includes a nebulizer operable to emit a cleaning mist into the hand-cleaning volume, a source of a cleaning solution in communication with an inlet of the nebulizer, and, preferably, a nebulizer vent disposed oppositely from the nebulizer across the hand-cleaning volume. The cleaning mist is in an activated state, such as a plasma gas or an ionized gas. Preferably, the cleaning mist is produced by passing a vapor of the cleaning solution through a plasma, to produce a dissociated, activated state in the cleaning mist. The activated cleaning mist thereafter passes across the hands received in the hand-cleaning volume.

The cleaning mist reacts with the chemical contaminants on the surface of the hand, mobilizes these contaminants, and causes them to vaporize and entrain in the flow of cleaning mist for removal from the system. The cleaning solution may be selected according to the type of contaminants that are expected in each application. In a typical case, however, organic contaminants are removed using an aqueous cleaning mixture of dissociated hydrogen peroxide, optionally an acid such as citric acid or lactic acid, and n-propyl alcohol. There may be, and preferably are, two or more cleaning solutions that are used sequentially to remove specific chemical contaminants. A skin conditioner may also be introduced in those cases where the hands are ungloved.

Biological agents may be removed by the cleaning mist, and/or a separate biological cleaning device such as an ultraviolet light source may be provided.

The apparatus further includes a controller operable to activate the mechanical-cleaning device and to activate the chemical-cleaning device and/or biological cleaning device during different time periods. In a typical situation, the mechanical-cleaning device is first operated for a period of time, typically 10 seconds or less, to dislodge particles. The chemical-cleaning device is then activated for a period of time, typically 10 seconds or less, to solubilize and remove chemical contaminants. The mechanical-cleaning device is then activated, to remove the condensed cleaning mist and any chemical contaminants dissolved in the condensed cleaning mist, by blowing them off the hand surface, and to dry the surface of the gloved or ungloved hand. If a second cleaning solution is to be used, the chemical-cleaning device is operated again using a second leaning solution, and the mechanical-cleaning device is thereafter operated to blow away any liquid on the surface, and to dry the surface. At the end of the cycle, the gloved or ungloved hand has been cleaned of particulate and chemical contaminants, and is dry and immediately ready for return to the activity being performed.

The apparatus is preferably placed in a housing, which has an opening therethrough which permits a person to place a gloved or ungloved hand (or both hands) into the hand-cleaning volume. The apparatus preferably includes a negative-pressure source within the housing adjacent to the opening, so that gas within the housing is preferentially drawn into the negative-pressure source rather than escapes through the opening. The negative-pressure source may be either the gas-source vent or the nebulizer vent, or a separate vent.

The method of the invention involves directing a flow of pressurized activated gas over the hand, and thereafter flowing a mist of a cleaning solution over the hand. The method is preferably, but not necessarily, performed in the apparatus described above. As will be discussed subsequently, the approach is highly flexible according to different cleaning requirements. An illustrative number of the approaches will be discussed subsequently.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
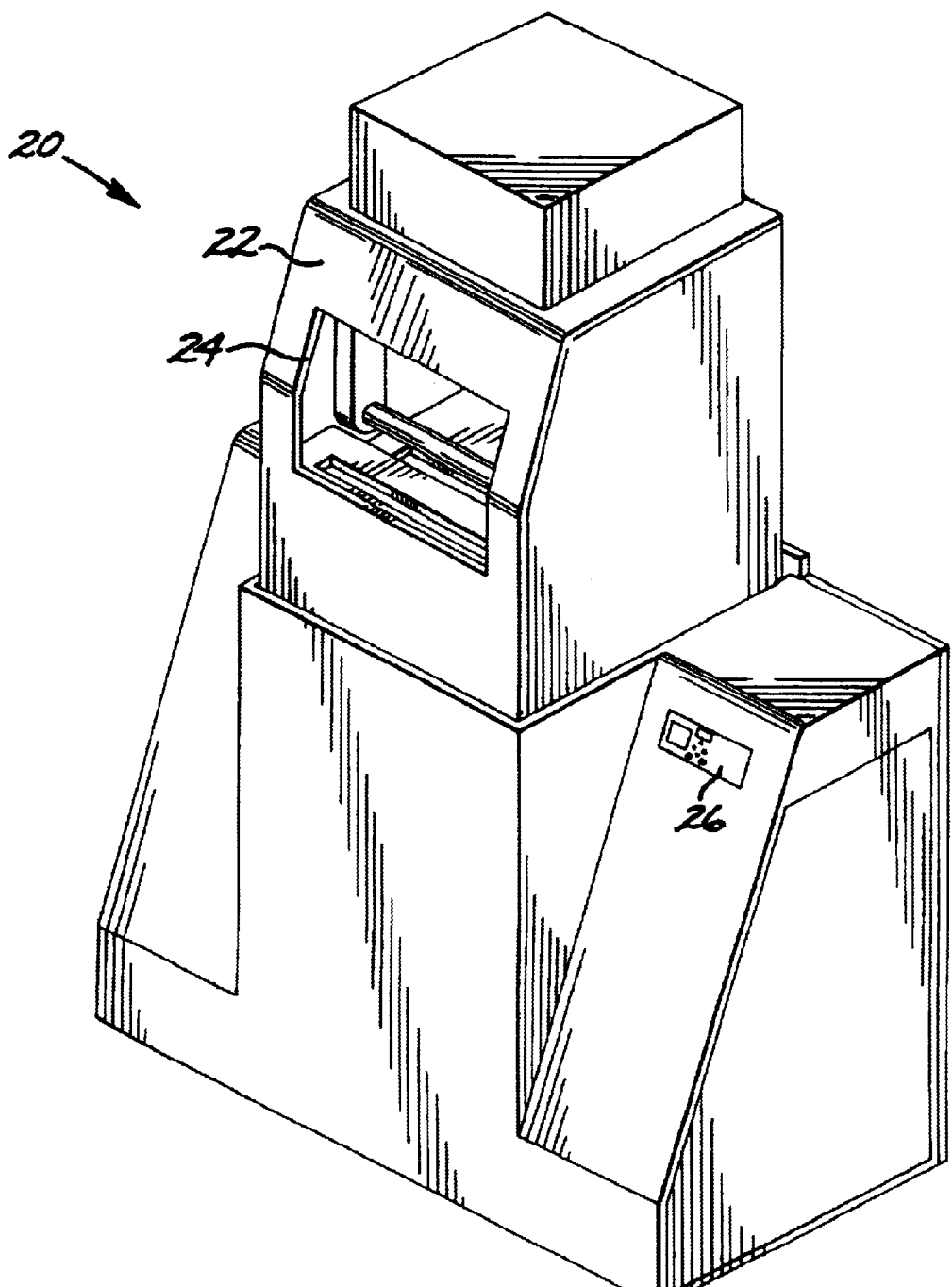
FIG. 1 is a schematic perspective front view of a housed apparatus according to the invention.
Figure 2:
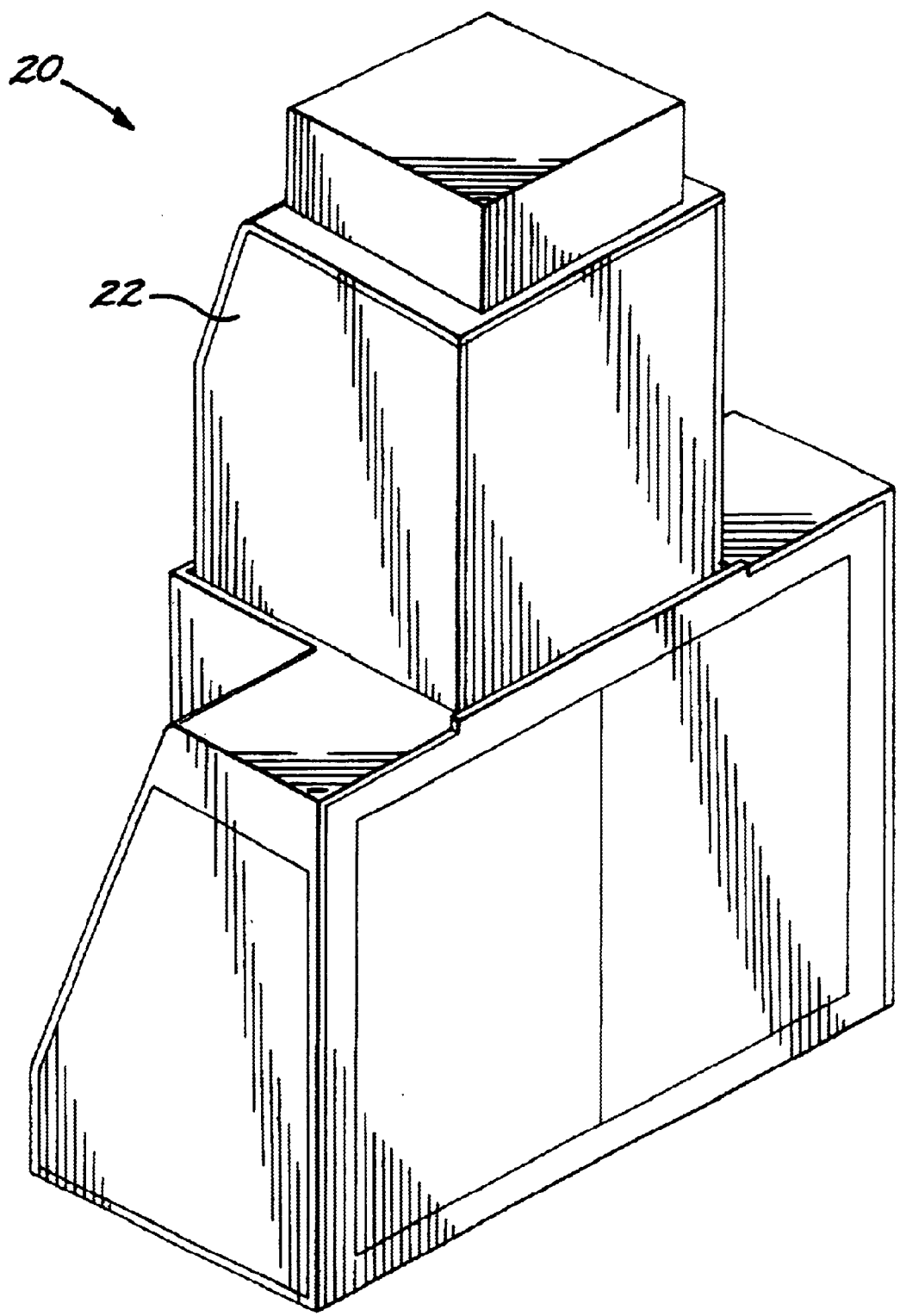
FIG. 2 is a schematic perspective rear view of the housed apparatus of FIG. 1.

FIGS. 1 and 2 are exterior views of a cleaning apparatus 20 for cleaning gloved or ungloved human hands. Where the hand is ungloved, the exposed human skin is cleaned. Where the hand is gloved, the gloves are preferably made of an elastomeric material such as natural latex or a synthetic elastomer. The apparatus 20 includes a housing 22 having an opening 24 therethrough. The opening 24 is sized to receive one or (preferably) two human hands and is positioned at a convenient height from the floor for insertion of the hand. In a prototype apparatus 20, the opening 24 is 9 inches high by 12 inches wide in size, and is about 43 inches from the floor. A control panel 26 is positioned on the front of the apparatus 20 for access by the user.

Figure 3:
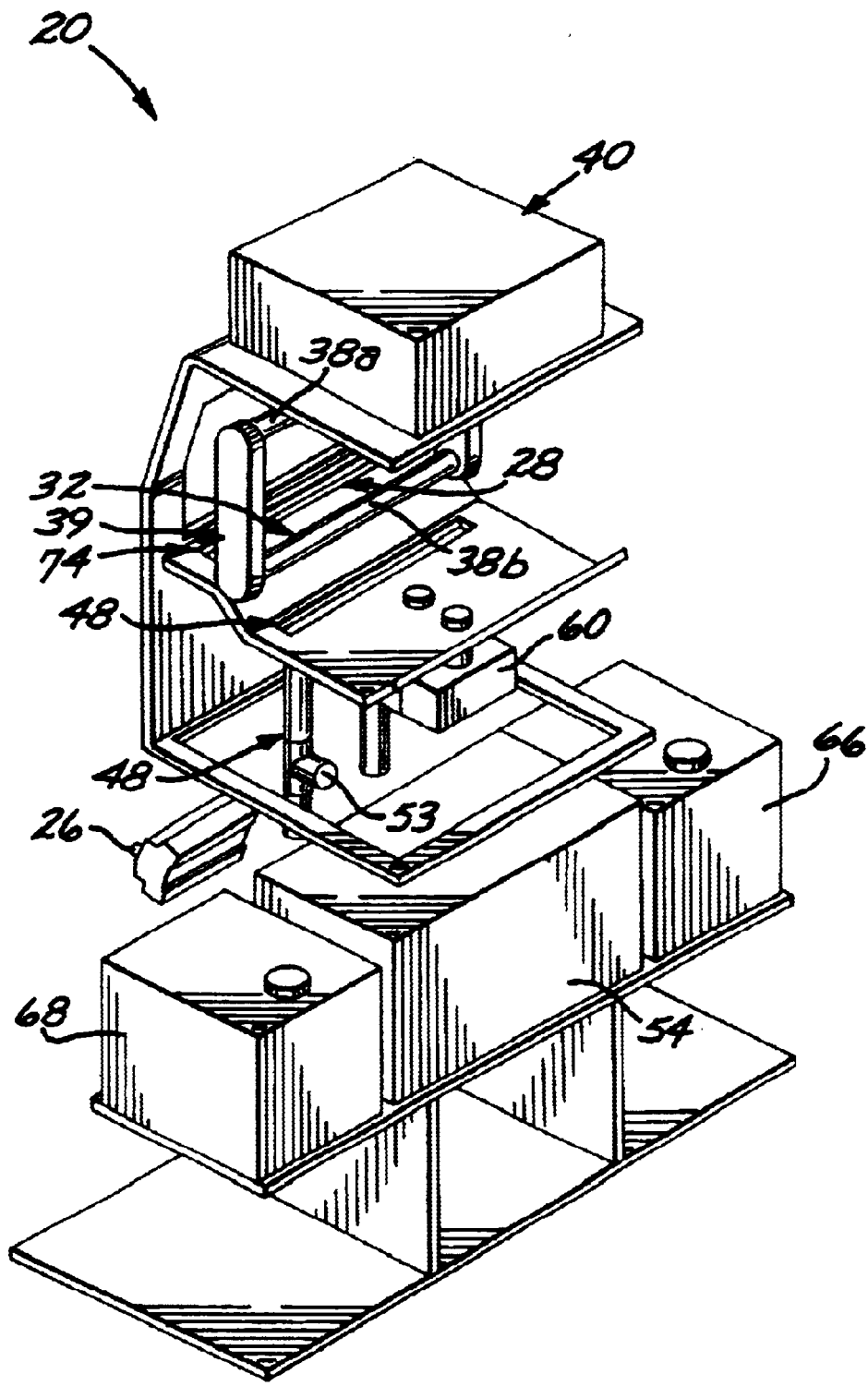
FIG. 3 is a schematic perspective rear interior view of the apparatus in the same view as FIG. 2, but with the housing removed to reveal the interior components.
Figure 4:
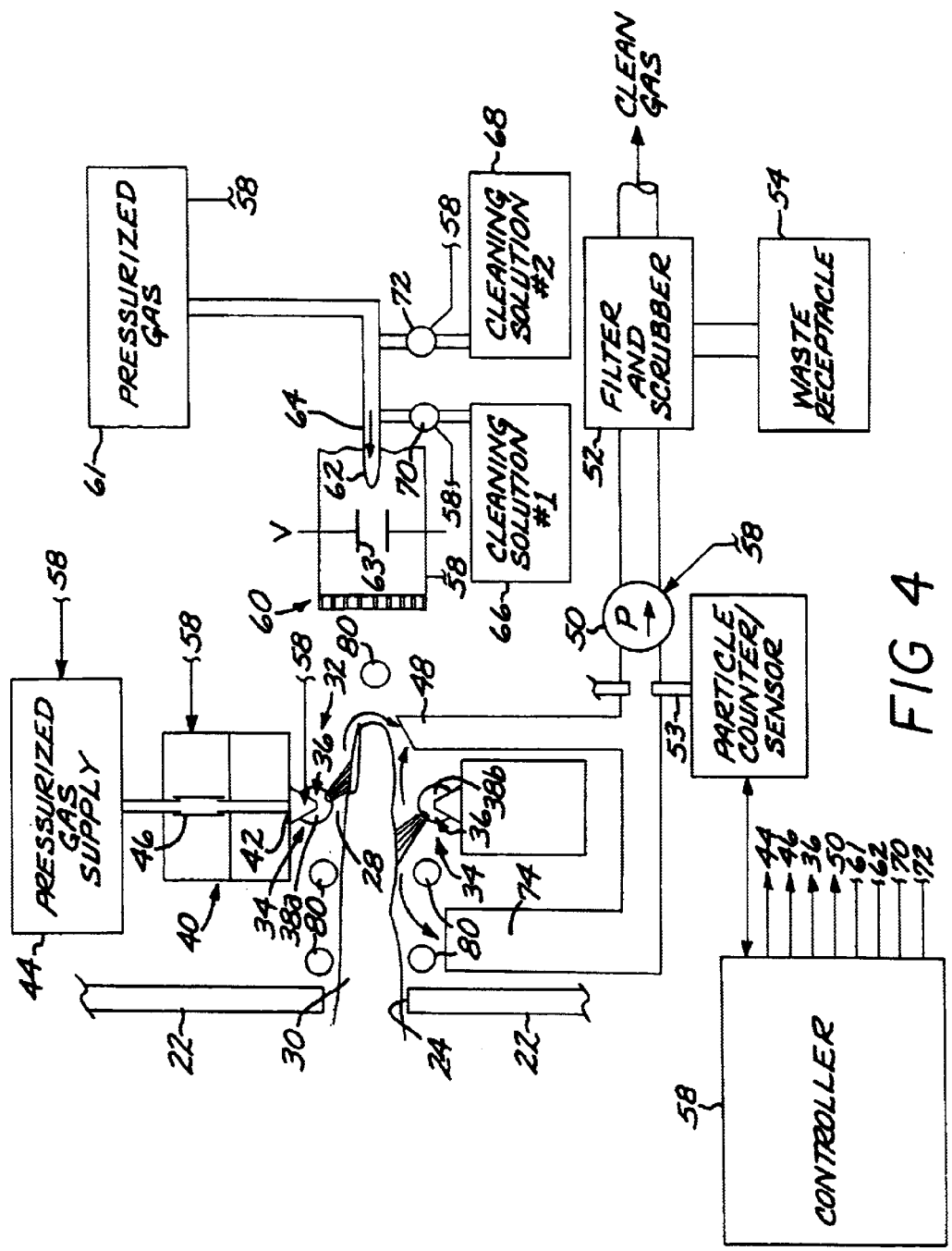
FIG. 4 is a schematic interior layout of the hand-cleaning volume and associated apparatus, with the mechanical-cleaning device operating.
Figure 5:
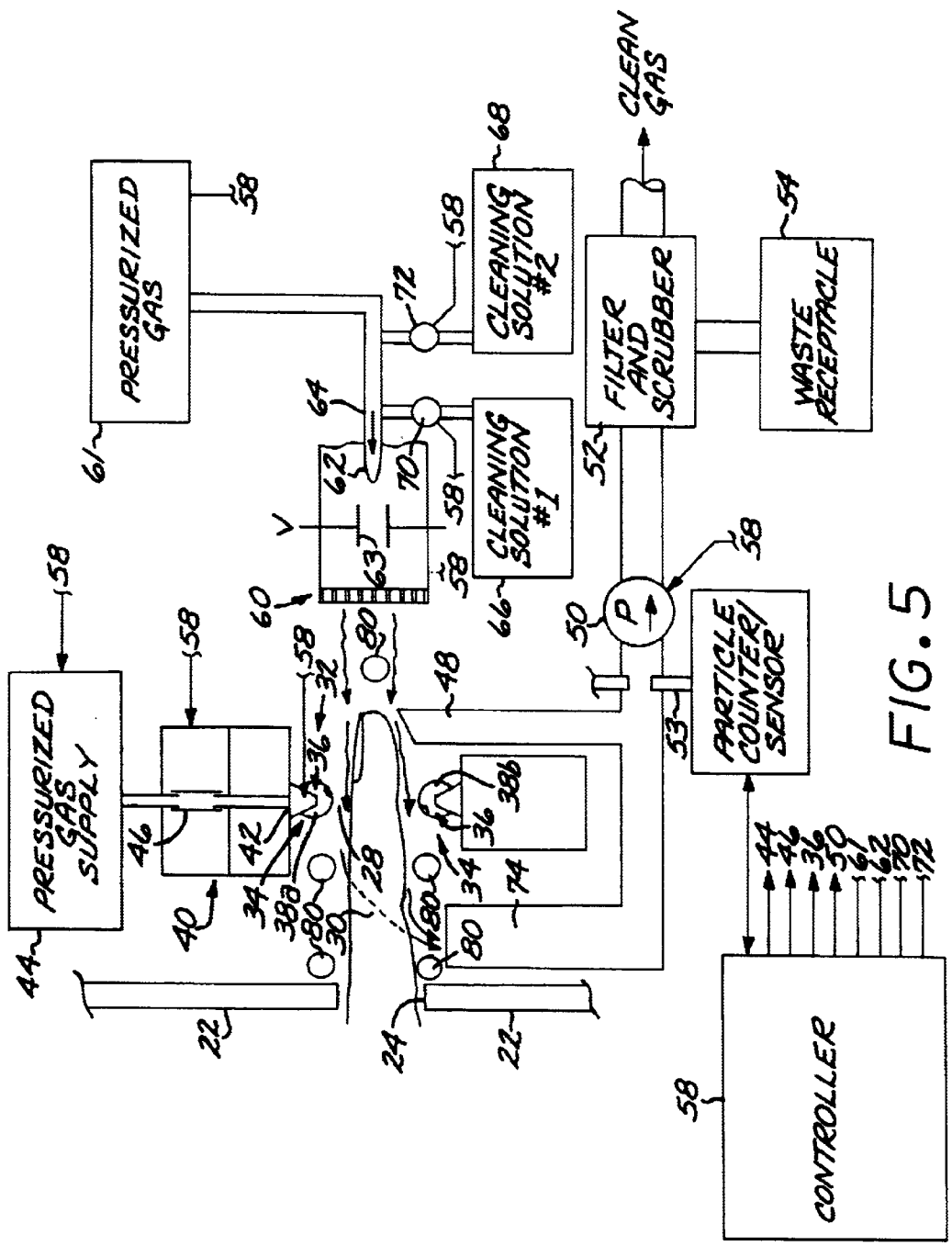
FIG. 5 is a schematic interior layout of the hand-cleaning volume and associated apparatus, with the chemical-cleaning device operating.

FIG. 3 is the same view as FIG. 2, but with the housing 22 removed so that the interior components are visible. FIGS. 4 and 5 are layouts of the interior of the apparatus with the housing removed, during different portions of the operating cycle.

The apparatus 20 has a hand-cleaning volume 28 sized to receive a gloved or ungloved human hand 30 therein, through the opening 24. The apparatus 20 comprises a mechanical-cleaning device 32 that dislodges particles from the surface of the gloved or ungloved hand. The mechanical-cleaning device 32 may be of any operable type that dislodges particles from the surface of the hand 30. The dislodging of particles is particularly important in some clean-room and medical applications where the hand is gloved. During storage, shipment, and use, elastomeric articles such as gloves typically develop small microcracks at the external surfaces thereof. Such microcracks are found in both natural latex and synthetic elastomers. These microcracks are not so large and deep as to cause the elastomeric glove to fail, and the microcracks are therefore acceptable in many uses of the articles. However, the surface microcracking of the elastomeric glove can lead to the production or retention of particulate material which can later fall from the article and lead to particulate-contamination problems in some environments, such as a clean room manufacturing environment or some medical environments. Some particulate is produced as the elastomeric material itself breaks away (spalls) from the surface. Additional particulate may be produced by particles that arise externally and are entrapped and retained within the microcracks as the user flexes the article, and then are released later to fall away from the elastomeric article. The mechanical-cleaning device 32 removes particles of both types from the surface of the glove.

The preferred mechanical-cleaning device 32 includes a pressurized gas source 34 positioned to direct a flow of pressurized gas into the hand-cleaning volume 28. The pressurized gas source 34 may be of any operable type. The preferred pressurized gas source 34 is a gas knife, preferably an air knife 36. The air knife 36 includes a first cylinder 38a mounted at the top of the hand-cleaning volume 28 and thence above the hand 30 and extending transversely thereto, and a second cylinder 38b mounted below the hand-cleaning volume 28 and thence below the hand 30 and extending transversely thereto. Each cylinder has an axis extending out of the plane of the drawing in FIGS. 4 and 5. Each cylinder 38a and 38b has nozzles therein, directed generally toward the gloved hand. Air or other gas flowing through the nozzles impinges upon the gloved or ungloved hand, mechanically dislodging loose particles from the glove surface. The cylinders 38a and 38b are rotary air knives and are driven by motors 39 or other types of drives to rotate about their axes, to sweep over the entirety of the top surface of the gloved or ungloved hand and the bottom surface of the gloved or ungloved hand, respectively. An array of fixed nozzles (not shown) may be used instead of or in addition to the air knife in some applications. The use of the gas knife as the pressurized gas source 34 is preferable to other types of gas sources such as an array of fixed nozzles where relatively high pressure cleaning is desired, because for a fixed total force on the hand of the user at any moment the gas knife approach allows a higher local pressure to be used to dislodge the particles.

A source of pressurized gas 40 is in communication with an inlet 42 of the pressurized gas source 34. The pressurized gas is preferably in an "activated state", meaning that it has been activated by an ionizing field or a plasma. Most preferably, the pressurized gas flowing from the source of pressurized gas 40 is in an ionized state. If in the ionized state, the activated gas may be in a balanced ionized state, meaning that it has approximately equal numbers of positive and negative ions, or in a highly ionized, unbalanced state, meaning that it has unequal numbers of positive and negative ions. The balanced ionized state is preferred. The source of pressurized gas 40, preferably a source of ionized air, includes a pressurized gas supply 44, such as a pressurized gas bottle, a fan, or a pumped tank. The pressurized gap supply 44 may supply gas at a constant pressure. More preferably, however, the pressurized gas supply 44 supplies a gas flow that is pulsed, so that the gas flowing out of the pressurized gas source 34 is pulsed. The pulsed gas is found to be more effective in dislodging the particles from the glove surface than is gas flowing at constant pressure. The gas pressure supplied to the pressurized gas source 34 is typically from about 30 psi to about 40 psi above atmospheric pressure, optionally pulsed between a maximum pressure of about 30–40 psi above atmospheric pressure and a minimum pressure of atmospheric pressure.

The mechanical dislodging of particles is further aided by a hand-washing motion and contacting of the two hands. The user rubs the hands together in the familiar hand washing movement used when hands are conventionally washed in soap and water, which flexes the gloves and causes particles to be dislodged. This movement may be performed during the operation of the pressurized gas source and also, if desired, during the subsequent operation of the chemical cleaning device. The result is a more effective ,removal of particulate from the glove surface.

Figure 6:
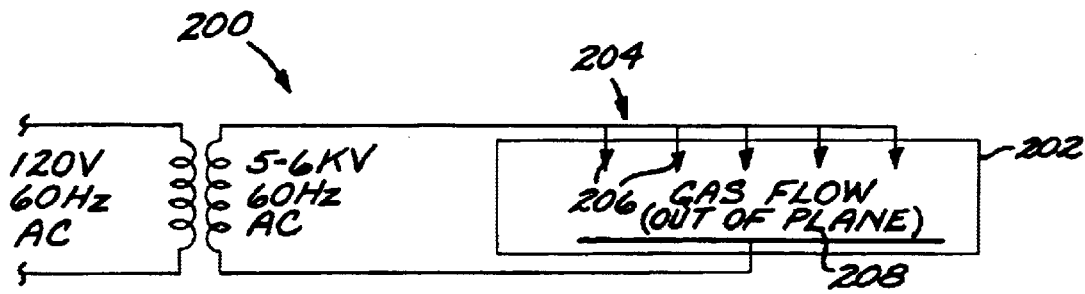
FIG. 6 is a schematic view of a comb-type ionizer used to produce balanced ionized gas in a pressurized-gas source.

Gas flowing from the source of pressurized gas 40 is activated before it reaches the pressurized gas source 34 by a gas activator 46 of any operable type, but which is here illustrated as a balanced gas ionizer. FIG. 6 schematically illustrates a comb-type balanced gas ionizer 200 which is preferably used as the gas activator 46. The gas to be ionized, typically air, flows in a gas flow channel 202 (in the direction out of the plane of the page in FIG. 6). A comb-type ionizer 204 has a plurality of sharp points 206, spaced about ½ inch apart, extending into one side of the gas flow channel 202. A conductive plane 208 extends into an opposing side of the gas flow channel. An AC voltage of about 5–6 kilovolts is applied to the points 206, producing a corona effect between the points 206 and the ground plane 20. A balanced state of ionization is imparted to the gas flowing in the gas flow channel 202. Alternatively, the gas may be ionized by any other suitable technique such as a laser or ultraviolet light. If the activated gas is a plasma, it may be created by a glow discharge in the manner to be discussed subsequently or any other suitable technique. In this embodiment, the gloved or ungloved hand is not exposed to the ionizing field or the plasma, but instead to the gas that has been activated and flows out of the nozzles in the cylinders 38. In a second embodiment to be discussed subsequently, the hands are in the plasma field. In most cases, the second embodiment will be used with gloved hands rather than ungloved hands.

A gas-source vent 48 communicates with the hand-cleaning volume 28. The gas-source vent 48 draws off the gas flow that is introduced by the mechanical-cleaning device 32. As seen in FIG. 4, a pump 50, typically in the form of an exhaust fan, draws the gas through the vent 48 and into a filter and scrubber 52. Clean gas is exhausted from the filter and scrubber 52, and the particulate waste that was entrained in the gas as a result of impacting the glove is deposited in a waste receptacle 54. The waste receptacle 54 is mounted in the apparatus 20 in the form of a drawer that may be removed easily for disposal of the waste (see FIG. 3).

A particle counter/chemical sensor 53 is optionally provided in the exhaust line between the gas-source vent 48 and the filter and scrubber 52. The particle counter/chemical sensor 53 may be of any operable type. The particle counter/chemical sensor 53 desirably gives particle counts and/or chemical constituents of the vented gas in real time. Preferably, the particle counter/chemical sensor 53 is a laser particle counter in the case of a particle counter. Such laser particle counters are known in the art, and are available commercially from Climet Instruments and the Met One Division of Pacific Scientific, for example. Other types of particle counters, such as white light particle counters or air filter systems, may also be used but are less preferred. Any type of real-time chemical sensor may be used which is appropriate to the expected type of chemical to be detected. The chemical sensor may be selected to measure specific chemical constituents or radioactive species, again depending upon the application. The chemical species to be sensed will depend upon the nature of the industry where the cleaning apparatus 20 is to be used.

A controller 58 controls the operation of the mechanical-cleaning device 32, both as to timing and selection of operating parameters. The controller 58 sends control signals to the pressurized gas supply 44, the gas ionizer 46, the drive of the air knife 36, and the pump 50. It also receives input from, and controls, the optional particle counter/chemical sensor 53. The controller 58 is preferably a microcomputer that is programmed to send command signals according to procedures discussed more fully subsequently, and to receive, store, and analyze data.

The apparatus 20 further includes a chemical-cleaning device 60. The chemical-cleaning device 60 removes chemical contaminants that may be adhered to the surface of the gloved or ungloved hand 30 of the user. FIG. 5 illustrates the apparatus 20 when the chemical-cleaning device 60 is in operation. The chemical-cleaning device 60 includes a nebulizer 62 (i.e., vaporizer) operable to emit a vapor of a cleaning mist into the hand-cleaning volume 28. The cleaning mist or vapor consists of droplets of the vaporized cleaning solution. The droplets are preferably roughly uniformly sized, on the order of from about 1 to about 20 micrometers in diameter. The nebulizer 62 preferably is a low-pressure, low-volume ultrasonic nebulizer, such as the commercially available Model SCA2000X made by Stultz. The ultrasonic energy introduced by this type of nebulizer also aids in dissociation of the molecules of the vaporized cleaning material, and lowers the electromagnetic energy required to achieve ionization of the molecules. A non-ultrasonic nebulizer may be used instead. The nebulizer may be a high-pressure, low-volume spray head that establishes ultrasonic waves in the vaporized cleaning material, leading to a higher dissociation and subsequent ionic activity. The nebulizer may instead be a spray system such as the IVEK Digispense 800 System. The gas that is to be vaporized by the nebulizer 62 is supplied from a pressurized gas source 61 communicating with an inlet 64 of the nebulizer 62. The pressurized gas source 61 may be of any operable type, such as a pressure bottle or a compressor-driven system.

In many cases, a separate nebulizer is provided for each cleaning solution (although only a single nebulizer is illustrated). A commercial nebulizer is typically tuned for the specific fluid to be vaporized into a mist, so that optimal vapor production occurs only for that specific fluid or closely similar fluids. If multiple cleaning solutions are used with substantially different properties, it is usually necessary to provide a separate nebulizer for each of the flows of cleaning solution.

Figure 7:
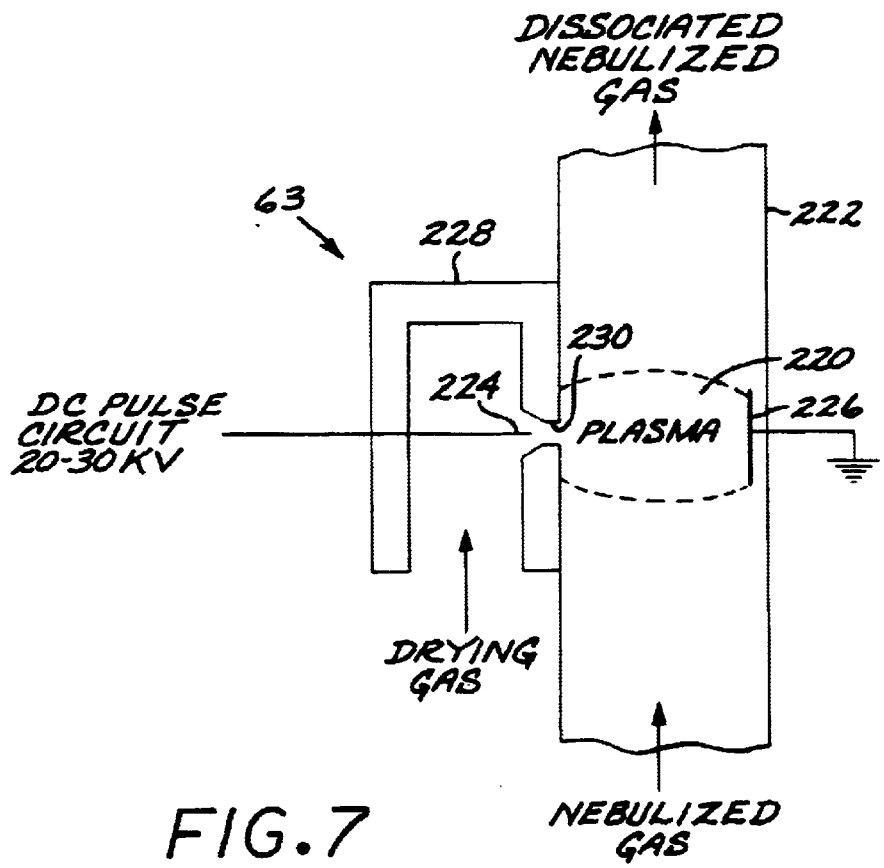
FIG. 7 is a schematic view of a glow-discharge plasma source used to activate a nebulized cleaning solution.

The nebulizer 62 produces a cleaning mist that may be, and preferably is, activated prior to the time that it reaches the hand-cleaning volume 28. That is, the gloved or ungloved hand is not exposed directly to the plasma or ionizing field, but only to the activated molecules of the cleaning mist after they leave the plasma or ionizing field. The cleaning mist may be activated by a plasma or an ionized field. The plasma state or the ionized state may be achieved by any operable techniques, but preferably a plasma source 63 as illustrated in FIGS. 4–5 and 7. As illustrated in FIG. 7, the plasma source 63 is a glow-discharge plasma source which produces a plasma 220 in a gas-flow channel 222. The nebulized gas flows through the plasma 220, resulting in activated, dissociated species in the nebulized gas. In the example of most interest to the inventors, the cleaning mist contains hydrogen peroxide, $H_2O_2$, as it enters the plasma 220. After it leaves the plasma, at least some of the hydrogen peroxide molecules have dissociated to produce hydroxyl (OH) and monatomic oxygen (O) activated species. These species remain dissociated for several seconds, during which time they flow to and over the hand 30. To achieve maximum cleaning efficiency, the plasma source 63 is preferably located as closely to the hand-cleaning volume 28 as possible, but not so close that the hands actually are within the plasma 220 in this embodiment. The dissociated species rapidly react chemical contaminants on the hand 30. The glow-discharge plasma source is presently preferred to other types of gas activating devices, as the residence time of the dissociated species in the dissociated state is longer.

The plasma 220 is produced by the current flow between an electrode 224 charged to about 20–30 kilovolts by a DC pulse circuit, and ground 226. The electrode 224 resides in a hydrophobic insulator 228 with access to the gas-flow channel 222 through an aperture 230. In development studies, the inventors observed a tendency to chemical attack of the electrode 224 by the moisture in the nebulized gas flowing in the gas-flow channel 222. To shield the electrode 224 and prevent such attack, a dry gas is introduced into the interior of the insulator 228 and flows around the electrode 224 and thence out of the aperture 230.

At least one source of a cleaning solution is in communication with the inlet 64 of the nebulizer 62. Preferably, there are at least two such sources, a first source 66 of a first cleaning solution and a second source 68 of a second cleaning solution. These sources are provided as removable tanks, such as shown in FIG. 3. No separate source hookups for chemicals are required for the apparatus 20, which may therefore be freestanding in a clean room or other setting (except for an electrical power source, which may be a battery). Pumps 70 and 72 pump cleaning solutions from the respective sources 66 and 68 to the inlet 64 of the nebulizer 62. The cleaning solutions are not introduced into the nebulizer 62 at the same time, but instead are introduced sequentially as will be described subsequently.

A wide variety of cleaning solutions may be used, depending upon the specific cleaning requirements. That is, the chemical substances to be removed from the hands in a clean room in the microelectronics industry may be quite different from the chemical substances to be removed from the hands in a hospital operating room. The following discussion is provided as illustrative of a presently preferred approach for general cleaning, but the use of the invention is not so limited.

In the cleaning of the glove surface of an elastomerically gloved hand, the first cleaning solution is an aqueous solution of hydrogen peroxide, EDTA (ethylenediaminetetraacetate), and n-propyl alcohol, in de-ionized water. The hydrogen peroxide is the primary source of the activated species, as discussed earlier. The EDTA chelates ions such as potassium and sodium, which aids in achieving sterilization of the glove. The n-propyl alcohol serves as a wetting agent and also promotes penetration of the cleaning mist into the surface of the glove. The second cleaning solution is an aqueous solution of hydrogen peroxide, n-propyl alcohol, and citric or lactic acid, in de-ionized water. The citric or lactic acid has a synergistic effect when mixed with hydrogen peroxide to achieve sterilization of microorganisms. The nebulized first cleaning solution is plasma activated, and the nebulized second cleaning solution is also plasma activated. Particle counting is normally conducted as part of the cleaning of gloves or other elastomeric articles, and chemical analysis is often performed.

In the cleaning of the hand surface of an ungloved hand, the first cleaning solution is hydrogen peroxide in deionized water. The second cleaning solution is a solution of lactic acid in de-ionized water, with the optional addition of n-propyl alcohol. The lactic acid serves to neutralize halides and to sterilize microorganisms. A hand conditioner such as aloe vera or a glycerine-based conditioner may be added to the second cleaning solution, or introduced to the ungloved hand in a separate step subsequent to the contacting with the second cleaning solution. In this case, the nebulized first cleaning solution is plasma activated, and the nebulized second cleaning solution is not plasma activated. Particle counting is not normally conducted as part of the cleaning of ungloved hands, but chemical analysis is often performed.

While the cleaning solutions are intended primarily to remove chemicals from the surfaces, they also may aid in removing particles. Particles are bound to surfaces by a variety of mechanisms, including polar ionic attraction, triboelectric forces, and van der Waals forces. The combination of the balanced ionized air of the air knife, the physical force of the gas flow of the air knife, and the neutralization of ionic attraction by the free radicals of the chemical cleaning solutions is effective in overcoming all of these binding forces and removing particles from the gloved or ungloved hands.

The cleaning mist emitted from the nebulizer 62 is forced through the hand-cleaning volume 28 by a fan of the nebulizer and past the gloved or ungloved hand 30. It is removed from the hand-cleaning volume 28 by an air current produced by a nebulizer vent 74. The cleaning mist is thereby contacted to the gloved or ungloved hand surface and removed. The air current is produced by a pump, which may be the same pump 50 that draws the gas through the gas source vent 48. The pump 50 pumps the cleaning mist, which may also carry contaminants removed from the glove, to the filter and scrubber 52.

The pump 50 and the opening 24 are sized such that the pump 50 creates a slight negative pressure within the hand-cleaning volume 28, as compared with atmospheric pressure external to the cleaning apparatus 20. Atmospheric air is therefore drawn into the opening 24 and thence through the pump 50, so that there is no escape of any of the internal gases—flowing from the gas source 34 or the nebulizer 62—into the surrounding air.

The controller 58 controls the operation of the pumps 70 and 72, the nebulizer 62, and the pressurized gas source 61.

Some applications, such as medical facilities including hospitals, doctor's offices, and dental offices, require that the gloved or ungloved hand be sterilized of microorganisms as well. FIGS. 4 and 5 illustrates an embodiment of the invention which measures and cleans the gloves of particulate, and simultaneously sterilizes the gloves of microorganisms present on its outer surface. A microorganism sterilizer 80 is disposed within the interior of the housing 22, proximate to the hand-cleaning volume 28 and thence to the gloved or ungloved hand 30. The microorganism sterilizer may be of any operable type that is compatible with the particle measurement and cleaning apparatus, such as an illustrated UV (ultraviolet) lamp. Suitable UV lamps are available commercially from Aqua Ultraviolet USA. The microorganism sterilizer may be of other types as well, such as an ozone source, or a sterilizing gas introduced through the nebulizer 62 or separately. Another form of sterilization may be accomplished by selection of the vaporized cleaning material. If hydrogen peroxide ($H_2O_2$) is used as the vaporized cleaning material, the ionizing energy of the activating plasma causes the molecules to dissociate to activated species, which are reactive to oxidize organic species and destroy microorganisms. The use of an ultrasonic nebulizer facilitates the dissociation.

The microorganism sterilization may be accomplished either before, simultaneously with, or after the particulate measurement and cleaning. This embodiment of FIGS. 4 and 5 allows personnel in medical and dental facilities to reuse gloves in an appropriate manner. Typically, gloves might be reused for multiple procedures with the same patient or procedure, but not reused with different patients. Nevertheless, the present approach would provide an increase in safety to prevent contamination, and an increase in efficiency through decreased glove disposal.

Figure 8:
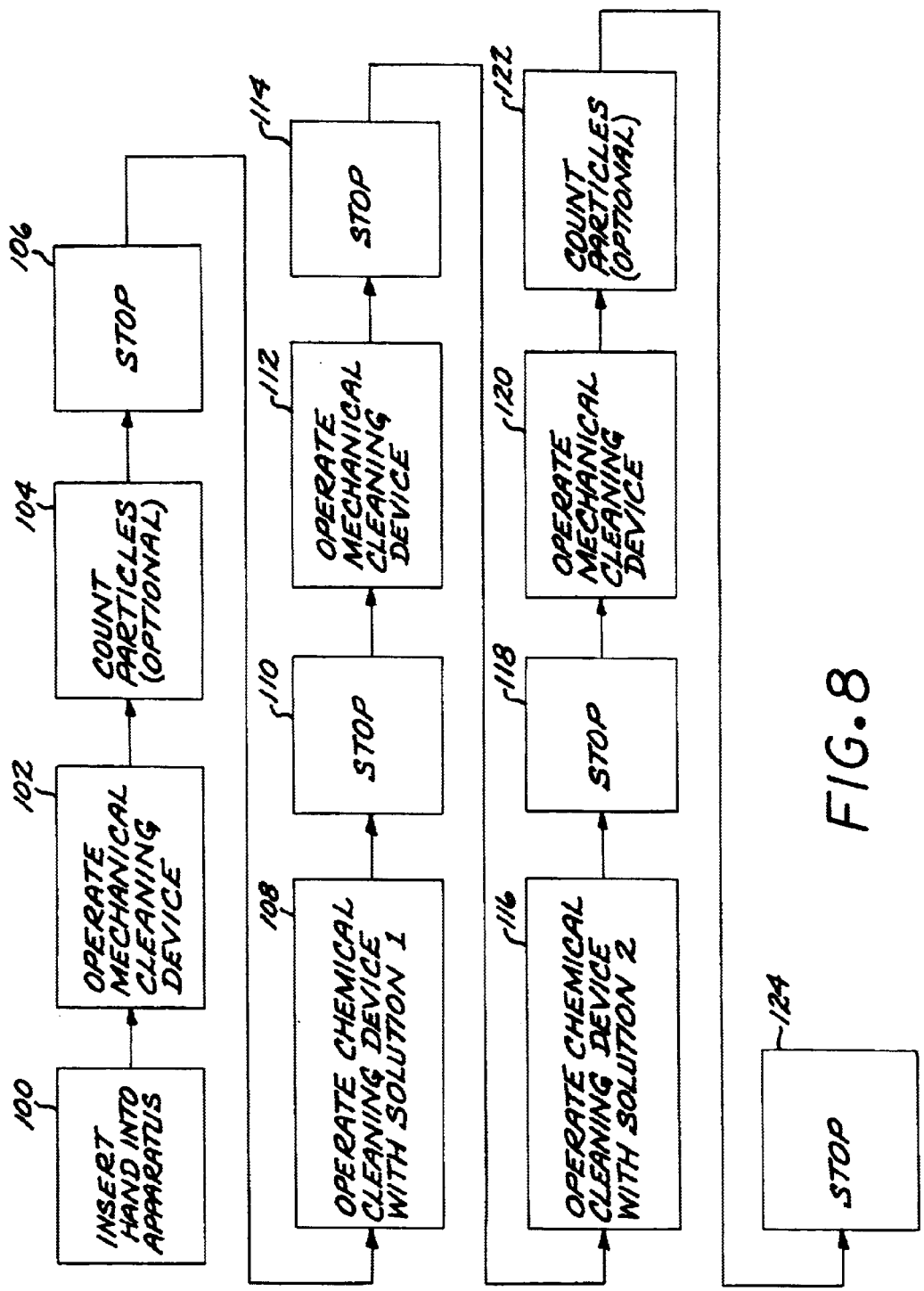
FIG. 8 is a block flow diagram of a preferred method for practicing the invention.
Figure 9:
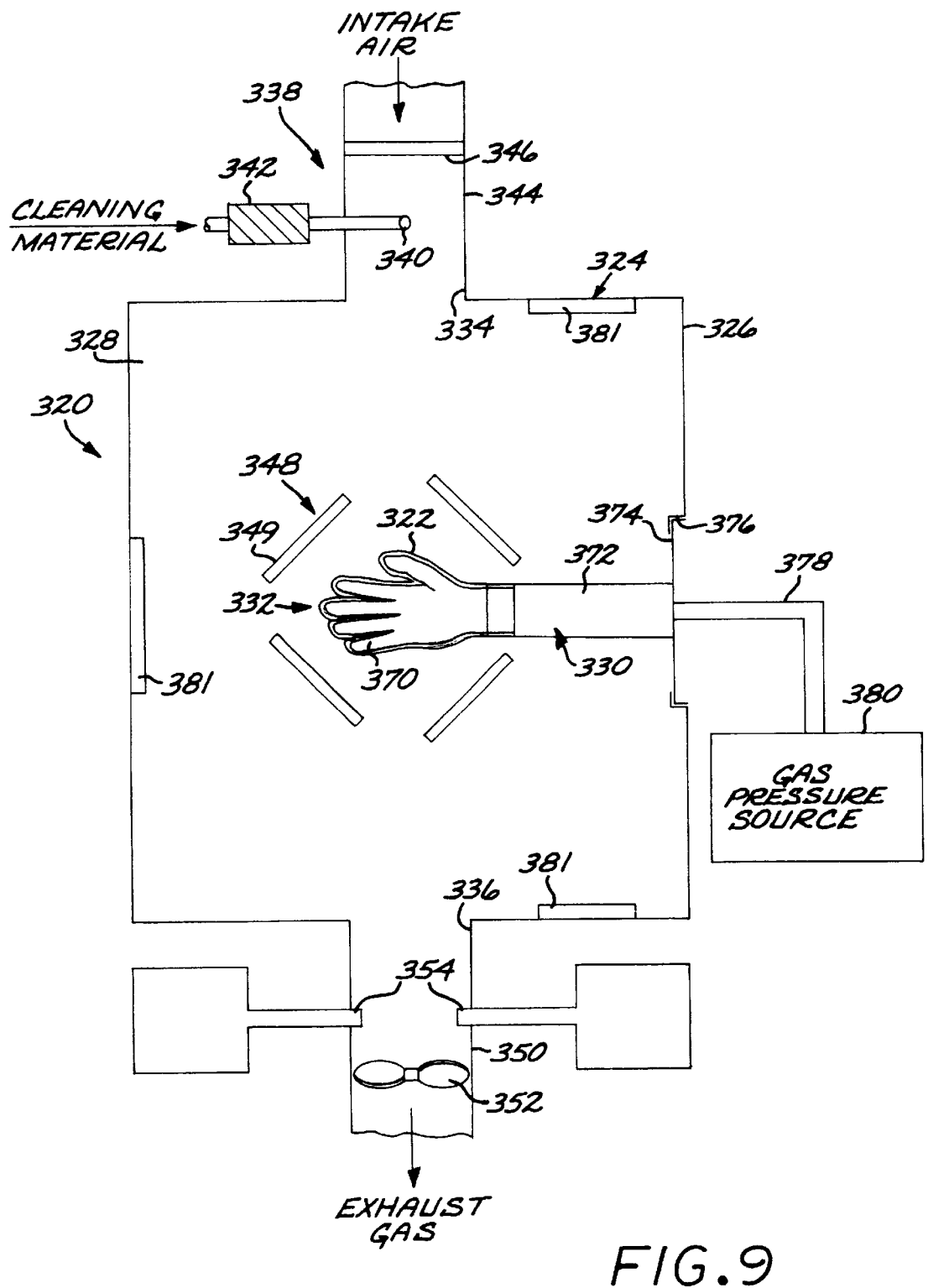
Figure 10:
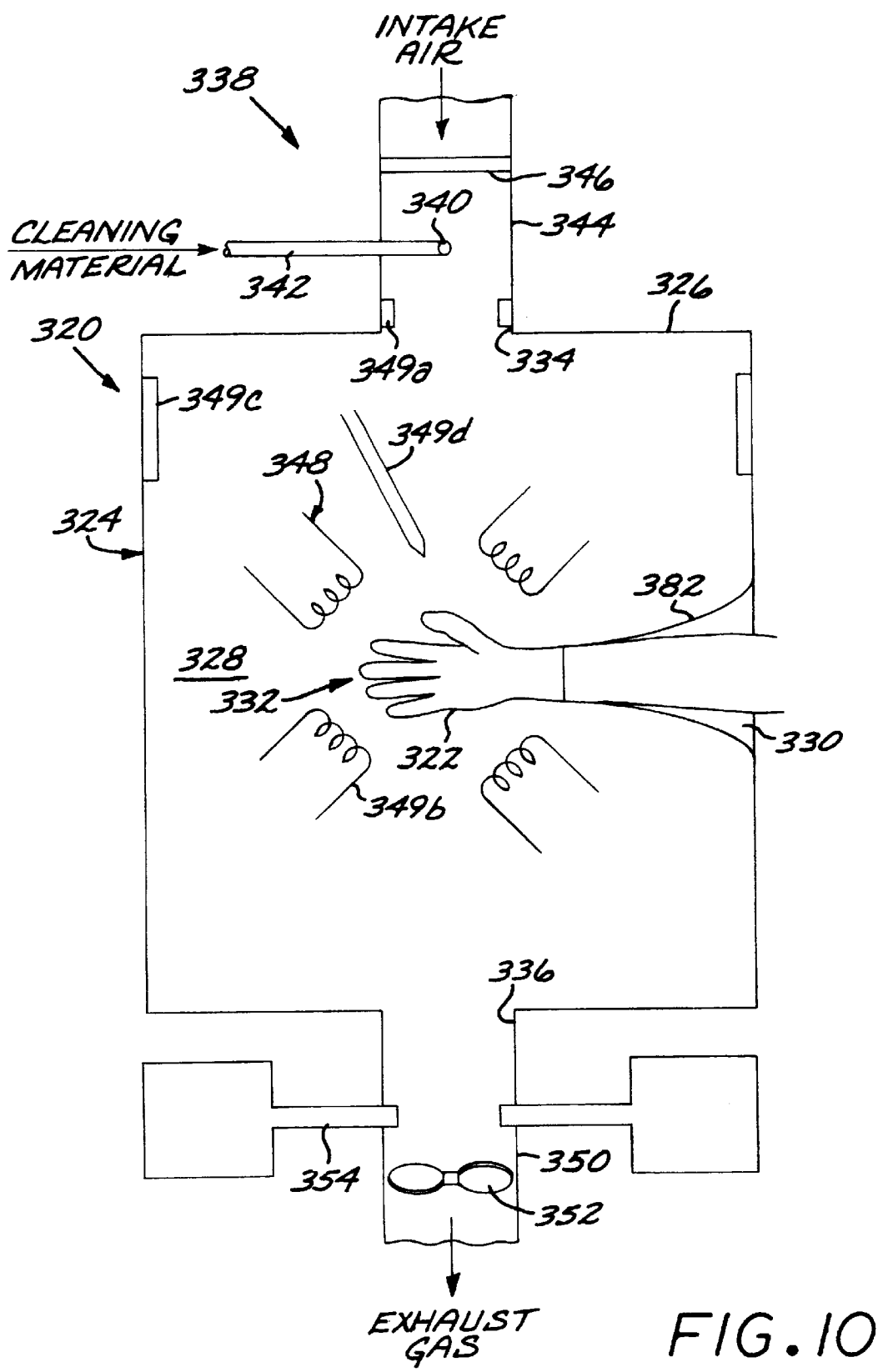
Figure 11:
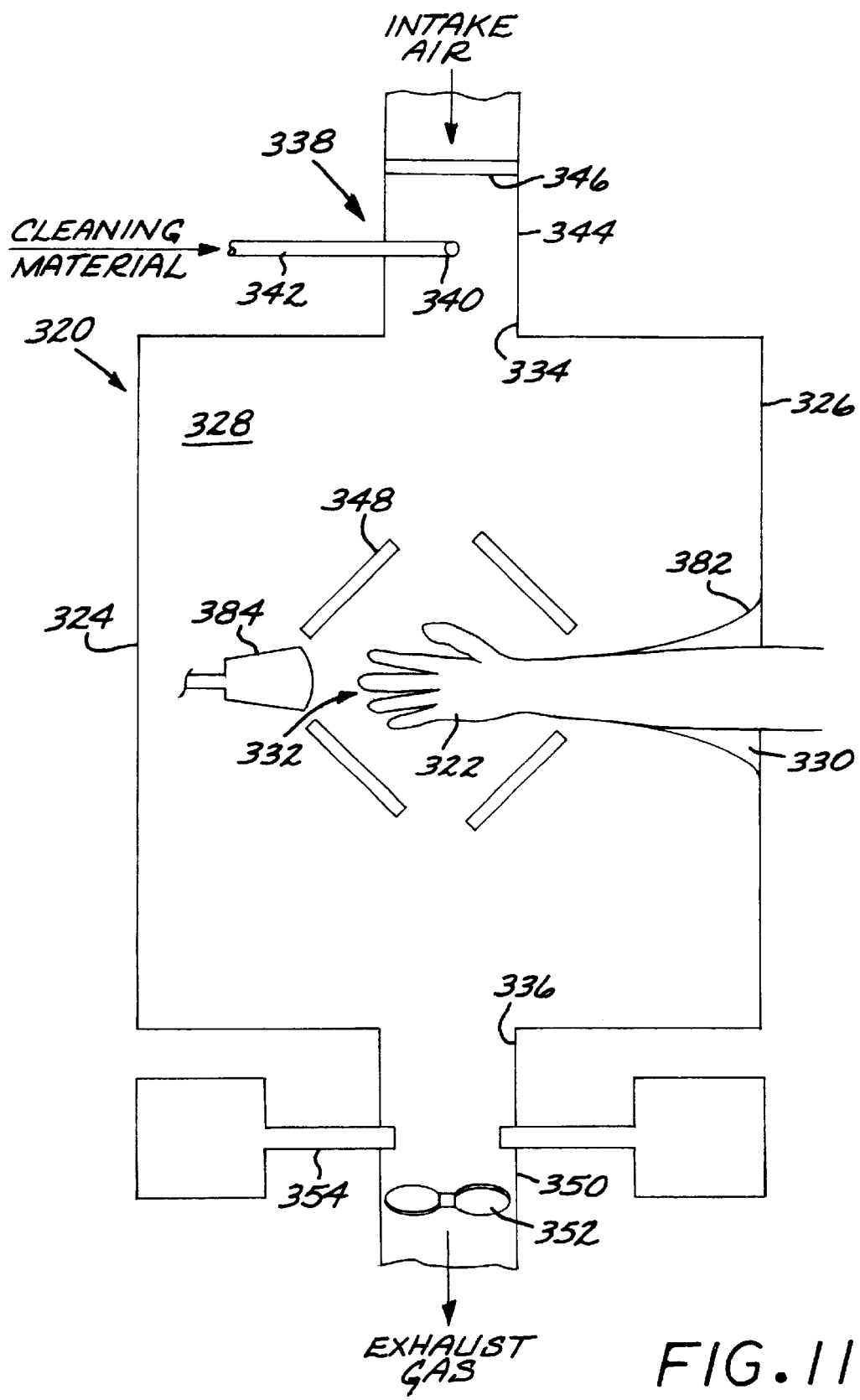
Figure 12:
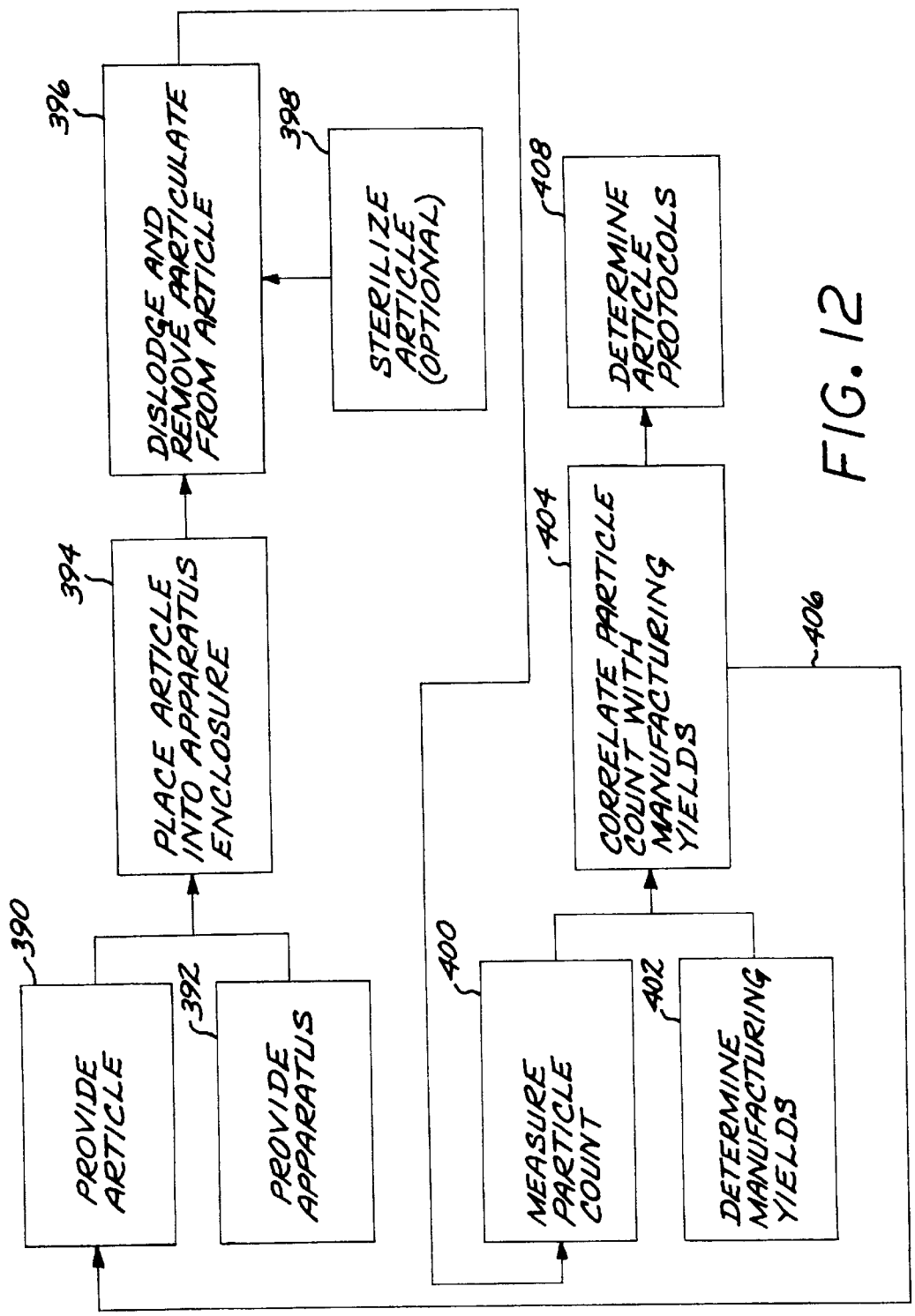

FIG. 8 depicts a preferred operating sequence for accomplishing cleaning of the gloves on the gloved hands of the user of the cleaning apparatus 20, where two cleaning solutions are used. The gloved or ungloved hands 30 are first inserted into the apparatus 20 through the opening 24, numeral 100. The machine may be activated by manual control of the user through the control panel 26 or a foot pedal, or automatically upon insertion by a photocell (not shown). The mechanical-cleaning device 32 is operated, numeral 102, to remove particles from the surfaces of the inserted gloves. Step 102 may continue for as long a period as necessary to accomplish a desired mechanical cleaning, but is typically from about 3 seconds to about 10 seconds. The optional particle counter/chemical sensor 53 may be operated, step 104, during this period or subsequently, but is typically operated simultaneously with the step 102. The mechanical-cleaning step 102 is completed and the mechanical-cleaning device 32 is stopped, numeral 106. Desirably, there is a break in time between the end of step 102 and the start of step 108, as indicated by the stop step 106. However, a brief overlap is permitted between the steps 102 and 108. The steps 102 and 108 may not be substantially overlapping in time, however, because the high gas flow rate from the pressurized gas source 34 would disrupt the contact of the nebulized cleaning mist with the glove. The same considerations are applicable for the other "stop" steps discussed herein.

The chemical-cleaning device 60 is thereafter operated using the first solution provided to the nebulizer 62, numeral 108. Step 108 may continue for as long a period as necessary to accomplish a desired chemical cleaning, but is typically from about 3 to about 10 seconds. The step 108 is stopped, numeral 110.

The mechanical-cleaning device 32 is again activated, numeral 112. This step blows off any residual first cleaning solution from the glove surface, dries the glove surface, and continues to dislodge any further particles from the glove surface that may have been freed during the chemical-cleaning step 108. Step 112 may continue for as long a period as necessary to accomplish a desired chemical cleaning, but is typically from about 3 to about 10 seconds. At the completion of step 112, the hands are dry. The particle counter/chemical sensor 53 may optionally be operated during or after this step 112. The step 112 is stopped, numeral 114.

If only a single cleaning solution is used, the cleaning operation is complete. If the second cleaning solution is used as well, the following steps are performed.

The chemical-cleaning device 60 is again operated, numeral 116, but this time the second cleaning solution is provided to the nebulizer 62. Step 116 may continue for as long a period as necessary to accomplish a desired chemical cleaning, but is typically from about 3 to about 10 seconds. The step 116 is stopped, numeral 118.

The mechanical-cleaning device 32 is again activated, numeral 120. This step blows off any residual second cleaning solution from the glove surface, dries the glove surface, and continues to dislodge any further particles from the glove surface that may have been freed during the chemical-cleaning step 116. Step 116 may continue for as long a period as necessary to accomplish a desired chemical cleaning, but is typically from about 3 to about 10 seconds. At the conclusion of step 116, the hands are dry. The particle counter/chemical sensor 53 may optionally be operated during or after this step 120, numeral 122. This particle count is a final particle count and any chemical analysis is a final chemical analysis. The steps 120 and 122 are stopped, numeral 124.

When ungloved hands are to be cleaned using the two cleaning solutions discussed earlier, it is preferred that only steps 100, 108, 110, 116, 118, 120, and 124 are performed. As discussed earlier, a separate step after step 120 may be added in which a skin conditioner is introduced into the hand-cleaning volume.

A prototype of the apparatus 20, constructed as shown in FIGS. 1–7, has been built and operated using the approach shown in FIG. 8. Tests using the mechanical cleaning device and the activated chemical cleaning device have demonstrated significant reductions in particles and chemical contaminants. New nitrile clean room gloves, for example, demonstrated a typical 38 percent reduction in particles of size equal to or greater than 0.5 micrometers after exposure to the cleaning cycle. Significant reductions of 10 percent to 30 percent were also seen in anion- and cation-extractable contamination. The same type of nitrile gloves showed reductions of up to 60 percent in particles of size equal to or greater than 0.5 micrometers when subjected to a controlled period of use prior to treatment in the cleaning cycle. For comparison, similar studies were run using the chemical cleaning device without plasma or ion activation of the nebulized cleaning solution. Those studies showed a typical 12 percent reduction in particles of size equal to or greater than 0.5 micrometers on new nitrile gloves. No consistent reductions were detected in anion- and cation-extractable contamination. The apparatus without the activation of the nebulized cleaning mist is therefore operable, but to a far lesser degree of effectiveness than where the nebulized cleaning mist is activated.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

What is claimed is:

1. A hand cleaning apparatus comprising:
   a hand-cleaning volume, the hand-cleaning volume being sized to receive a human hand;
   a mechanical-cleaning device, including
      a pressurized gas source positioned to direct a flow of pressurized gas into the hand-cleaning volume,
      a source of pressurized gas in communication with an inlet of the pressurized gas source,
      a pressurized gas activator intermediate the source of pressurized gas and said pressurized gas source, and
      a gas-source vent communicating with the hand-cleaning volume and being operable to remove pressurized gas from the hand-cleaning volume;
   a chemical-cleaning device, including
      a first source of a first cleaning solution
      an activating nebulizer operable to emit an activated cleaning mist into the hand-cleaning volume, the activating nebulizer including
         a vaporizer which creates a mist of the first cleaning solution,
         an activator which activates the mist of the first cleaning solution, the activator being selected from the group consisting of a plasma source and an ionizer, the vaporizer and the activator being located outside of the hand-cleaning volume, and
      means for causing the activated mist of the first cleaning solution to flow into the hand-cleaning volume; and
   a controller operable to activate the mechanical-cleaning device and to activate the chemical-cleaning device in response to the receipt of a human hand in the hand-cleaning volume and during different time periods in which a human hand is present in the hand-cleaning volume.

2. The apparatus of claim 1, wherein the source of the pressurized gas is a source of balanced ionized air.

3. The apparatus of claim 1, wherein the apparatus further includes at least one of a particle counter and chemical sensor in communication with the hand-cleaning volume.

4. The apparatus of claim 1, wherein the activated cleaning mist is selected form the group consisting of an ionized cleaning mist and a plasma-activated cleaning mist.

5. The apparatus of claim 1, wherein the source of the cleaning solution comprises a source of hydrogen peroxide.

6. The apparatus of claim 1, further including a housing, and an opening in the housing, the opening being sized to permit a person to place a hand into the hand-cleaning volume.

7. The apparatus of claim 6, further including a negative-pressure source within the housing adjacent to the opening, whereby gas within the housing is preferentially drawn into the negative-pressure source rather than escape through the opening.

8. The apparatus of claim 1, wherein the chemical-cleaning device further includes a second source of a second cleaning solution in communication with the inlet of the nebulizer, and wherein the controller is further operable to activate the mechanical-cleaning device, the chemical-cleaning device using the first source of the first cleaning solution, and the chemical-cleaning device using the second source of the second cleaning solution during different time periods.

9. The apparatus of claim 8, wherein the second source of the second cleaning solution comprises a source of an aqueous second mixture of disodium ethylenediaminetetraacetate and a surfactant.

10. The apparatus of claim 1, wherein the first cleaning solution comprising hydrogen peroxide.

11. A method for cleaning a hand, comprising the steps of directing a flow of pressurized activated gas over the hand, and thereafter flowing a mist of an activated cleaning mist of a cleaning solution over the hand, the activated cleaning mist being selected from the group consisting of an ionized cleaning mist and a plasma cleaning mist.

12. The method of claim 11, wherein the activated gas is selected from the group consisting of an ionized gas and a plasma-activated gas.

13. The method of claim 11, wherein the cleaning solution comprises a source of hydrogen peroxide.

14. The method of claim 11, including an additional step, after the step of flowing a mist, of flowing a second mist of a second cleaning solution over the hand.

15. The method of claim 14, wherein the second cleaning solution comprises a source of an aqueous second mixture of disodium ethylenediaminetetraacetate and a surfactant.

* * * * *